United States Patent
Jang et al.

(10) Patent No.: US 9,439,614 B2
(45) Date of Patent: Sep. 13, 2016

(54) X-RAY GENERATION MODULE, X-RAY IMAGING APPARATUS, AND X-RAY IMAGING METHOD

(71) Applicant: SAMSUNG ELECTRONICS CO., LTD., Suwon-si (KR)

(72) Inventors: Kwang Eun Jang, Busan (KR); Young Hun Sung, Hwaseong-si (KR); Jae Hak Lee, Yongin-si (KR); Jong Ha Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 287 days.

(21) Appl. No.: 14/055,361

(22) Filed: Oct. 16, 2013

(65) Prior Publication Data

US 2014/0112434 A1 Apr. 24, 2014

(30) Foreign Application Priority Data

Oct. 19, 2012 (KR) .................. 10-2012-0116950

(51) Int. Cl.
*A61B 6/04* (2006.01)
*A61B 6/00* (2006.01)
*A61B 6/03* (2006.01)

(52) U.S. Cl.
CPC .................. *A61B 6/502* (2013.01); *A61B 6/03* (2013.01); *A61B 6/488* (2013.01); *A61B 6/542* (2013.01)

(58) Field of Classification Search
CPC ...... A61B 6/502; A61B 6/4007; A61B 6/03; A61B 6/542; A61B 6/488
USPC .................................................. 378/9, 21, 37
See application file for complete search history.

(56) References Cited

U.S. PATENT DOCUMENTS

| 2008/0101547 | A1* | 5/2008 | Curtis | A61B 6/4476 378/198 |
| 2012/0219109 | A1* | 8/2012 | Albanese | A61B 6/02 378/37 |

FOREIGN PATENT DOCUMENTS

| KR | 1020080002762 A | 1/2008 |
| KR | 1020110026288 A | 3/2011 |
| KR | 1020110133666 A | 12/2011 |
| KR | 1020120010639 A | 2/2012 |

* cited by examiner

*Primary Examiner* — Courtney Thomas
(74) *Attorney, Agent, or Firm* — Sughrue Mion, PLLC

(57) ABSTRACT

Disclosed is an X-ray imaging apparatus, which includes a plurality of X-ray generation modules configured to emit X-rays to a subject, the X-ray generation modules being configured to move independently of one another, an X-ray detector configured to detect a plurality of X-rays emitted from the plurality of X-ray generation modules and which have passed through the subject, and an image processor configured to acquire a plurality of X-ray images from the plurality of detected X-rays.

25 Claims, 14 Drawing Sheets

FIG.6(a)

| THICKNESS (mm) | IMAGE-CAPTURE ANGLE |
|---|---|
| ~ 45 | 20° |
| 46 ~ 55 | 40° |
| 56 ~ 75 | 60° |
| 76 ~ | 80° |

FIG.6(b)

| DENSITY(%) | 20 ~ 30 | 31 ~ 40 | 41 ~ 60 | 61 ~ |
|---|---|---|---|---|
| IMAGE-CAPTURE ANGLE | 20° | 40° | 60° | 80° |

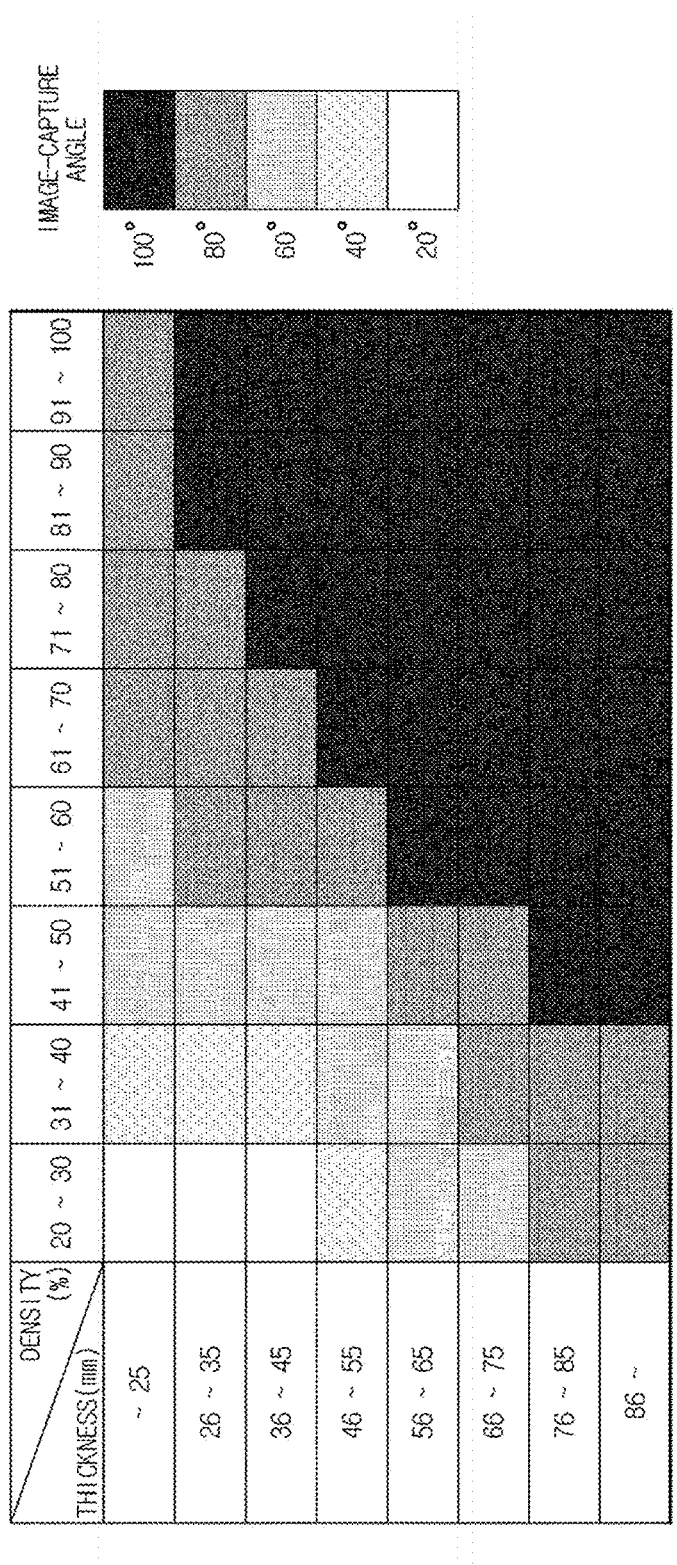

FIG.7(a)

| THICKNESS (mm) | NUMBER OF IMAGE-CAPTURE OPERATIONS |
|---|---|
| ~ 45 | 17 |
| 46 ~ 55 | 21 |
| 56 ~ 75 | 25 |
| 76 ~ | 29 |

FIG.7(b)

| DENSITY(%) | 20 ~ 30 | 31 ~ 40 | 41 ~ 60 | 61 ~ |
|---|---|---|---|---|
| NUMBER OF IMAGE-CAPTURE OPERATIONS | 17 | 21 | 25 | 29 |

X-RAY GENERATION MODULE, X-RAY IMAGING APPARATUS, AND X-RAY IMAGING METHOD

CROSS-REFERENCE TO RELATED APPLICATION

This application claims the benefit of Korean Patent Application No. 10-2012-0116950, filed on Oct. 19, 2012 in the Korean Intellectual Property Office, the disclosure of which is incorporated herein by reference in its entirety.

BACKGROUND

1. Field

Exemplary embodiments of the present disclosure relate to an X-ray generation module for generation and emission of X-rays, and an X-ray imaging apparatus and an X-ray imaging method which generate an X-ray image by transmitting X-rays through a subject and perform Automatic Exposure Control (AEC) using a plurality of X-ray generation modules.

2. Description of the Related Art

An X-ray imaging apparatus is an apparatus that diagnoses internal diseases of a subject by emitting X-rays to the subject and acquiring an image from X-rays having passed through the subject. X-ray imaging apparatuses which capture an image concentrated on an area of a human body have been marketed.

One example of an X-ray imaging apparatus which captures an image concentrated on any one area of a human body is a mammography system. The mammography system acquires a 2-Dimensional (2D) X-ray image of a breast by emitting X-rays to a compressed breast.

The mammography system may be advantageous to detect breast diseases at low cost, but has difficulty in distinguishing mass from other tissues in the acquired 2D X-ray image. In particular, upon image capture of a dense breast, an inspector (e.g., a medical professional) of the acquired 2D X-ray image is limited in his or her ability to distinguish diseases from internal tissues of the breast using only the acquired 2D X-ray image because the tissues overlap one another.

To overcome such limitations, a tomosynthesis system has been devised, which captures images of a compressed breast at different angles while moving an X-ray generator that generates X-rays, thereby acquiring a 3D X-ray image.

The tomosynthesis system employs a step-and-shoot method or a continuous-scan method, in order to acquire a plurality of 2D X-ray images as a single X-ray generator emits X-rays from several positions.

In the step-and-shoot method, 2D X-ray images are acquired as the X-ray generator, which is adapted to sequentially pass several image-capture positions, emits X-rays after stopping at the respective image-capture positions. In the continuous-scan method, 2D X-ray images are acquired as the X-ray generator continuously emits X-rays at several image-capture positions while rotating.

However, the step-and-shot method may cause shaking of the X-ray generator due to a damping motion of the X-ray generator that becomes heavy when the X-ray generator stops at the respective image-capture positions during X-ray emission, resulting in a blurred 2D image. The continuous-scan method also causes a blurred 2D image due to movement of the X-ray generator as the X-ray generator emits X-rays while moving.

Further, the tomosynthesis system captures images of a breast at various angles and composes 2D images acquired through respective captured images to form a 3D image. Thus, although the tomosynthesis system easily detects diseases as compared to the mammography system, the tomosynthesis system may require a plurality of X-ray emissions, which causes a problem in regard to patient radiation exposure.

Accordingly, in the tomosynthesis system, it may be important to appropriately set imaging conditions, such as an image-capture angle of a breast, in such a way as to limit patient radiation exposure while detecting diseases of the patient without errors.

SUMMARY

It is an aspect of the exemplary embodiments to provide a plurality of X-ray generation modules that are movable independently of one another, and an X-ray imaging apparatus and an X-ray imaging method using the X-ray generation modules, which may acquire 2D and 3D X-ray images free from blurring due to movement of the X-ray generation modules.

It is another aspect of the exemplary embodiments to provide an X-ray imaging apparatus and an X-ray imaging method, which set imaging conditions by reflecting properties of tissues of a subject.

Additional aspects of the exemplary embodiments will be set forth in part in the description which follows and, in part, will be obvious from the description, or may be learned by practice of the exemplary embodiments.

In accordance with one aspect of the exemplary embodiments, an X-ray imaging apparatus includes a plurality of X-ray generation modules configured to emit X-rays to a subject, the X-ray generation modules being configured to move independently of one another, an X-ray detector configured to detect a plurality of X-rays emitted from the plurality of X-ray generation modules and which have passed through the subject, and an image processor configured to acquire a plurality of X-ray images from the plurality of detected X-rays.

The X-ray imaging apparatus may further include a main body, and a transfer rail secured to the main body, and the plurality of X-ray generation modules may be configured to move on the transfer rail.

Each of the X-ray generation modules may include a moving unit configured to move each X-ray generation module independently.

The transfer rail may include a rack gear, and a guide protrusion to guide movement of the plurality of X-ray generation modules, the moving unit of each X-ray generation module may include a pinion gear engaged with the rack gear, and a transfer motor to rotate the pinion gear, and each X-ray generation module may have a guide groove into which the guide protrusion is fitted.

In accordance with another aspect of the exemplary embodiments, an X-ray imaging apparatus includes a plurality of X-ray generation modules configured to emit X-rays to a subject, the X-ray generation modules being configured to move independently of one another, an X-ray detector configured to detect X-rays emitted from the plurality of X-ray generation modules and which have passed through the subject, an image processor configured to acquire a plurality of X-ray images from the plurality of detected X-rays, and a controller configured to independently move the respective X-ray generation modules so as to enable the plurality of X-ray generation modules to irradiate the subject with X-rays at different positions.

In accordance with another aspect of the exemplary embodiments, an X-ray imaging apparatus includes a main body, a transfer rail secured to the main body, and a plurality of X-ray generation modules configured to emit X-rays to a subject, the X-ray generation modules being configured to move independently of one another along the transfer rail.

In accordance with another aspect of the exemplary embodiments, an X-ray imaging apparatus includes a plurality of X-ray generation modules configured to emit X-rays to a subject, the X-ray generation modules being configured to move independently of one another, an X-ray detector configured to detect a plurality of X-rays emitted from the plurality of X-ray generation modules and which have passed through the subject, an image processor configured to acquire a plurality of X-ray images from the plurality of detected X-rays, and a controller configured to set image-capture conditions based on at least one of a thickness and a density of the subject, and configured to move at least one X-ray generation module among the plurality of X-ray generation modules according to the image-capture conditions, thereby controlling an image capture operation to capture an image of the subject.

In accordance with another aspect of the exemplary embodiments, an X-ray generation module includes a housing in which a plurality of electronic parts configured to generate X-rays to be emitted to a subject and connection wires connecting the plurality of electronic parts are accommodated, and a moving unit configured to move the housing along a transfer rail independently of movement of another X-ray generation module that is movable along the transfer rail.

In accordance with a further aspect of the exemplary embodiments, an X-ray imaging method includes checking a thickness of a subject, performing a pre-shot by emitting X-rays from at least one X-ray generation module, among a plurality of X-ray generation modules that are movable independently of one another, to the subject, and acquiring a pre-shot image of the subject based on the pre-shot, determining a density of the subject by analyzing the acquired pre-shot image, setting image-capture conditions for a main-shot based on at least one of the thickness and density of the subject, and performing the main-shot by moving the at least one X-ray generation module among the plurality of X-ray generation modules according to the image-capture conditions, and acquiring a main-shot image based on the main-shot.

The image-capture conditions may include an image-capture angle, an image-capture position, and a number of image-capture operations.

The image-capture angle may be set to a greater value as the thickness of the subject increases, and may be set to a smaller value as the thickness of the subject decreases.

The image-capture angle may be set to a greater value as the density of the subject increases, and may be set to a smaller value as the density of the subject decreases.

The image-capture angle may be set to a greater value as the thickness of the subject increases and the density of the subject increases, and may be set to a smaller value as the thickness of the subject decreases and the density of the subject decreases.

The number of image-capture operations may be set to a greater value as the thickness of the subject increases, and may be set to a smaller value as the thickness of the subject decreases.

The number of image-capture operations may be set to a greater value as the density of the subject increases, and may be set to a smaller value as the density of the subject decreases.

The number of image-capture operations may be set to a greater value as the thickness of the subject increases and the density of the subject increases, and may be set to a smaller value as the thickness of the subject decreases and the density of the subject decreases.

A distance between two neighboring image-capture positions in a central region may be set to be different as compared to a distance between two neighboring image-capture positions in a peripheral region of an image capture angular range.

The image-capture positions may be set such that the distance between the two neighboring image-capture positions in the central region is smaller than the distance between the two neighboring image-capture positions in the peripheral region.

The magnitude of a tube voltage and a filter material in the central region may be set to be different as compared to a magnitude of a tube voltage and a filter material in the peripheral region.

The image-capture conditions may further include an anode material.

The density may be determined using a histogram of the pre-shot image.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 6(a) is a table illustrating image-capture angles depending on the thickness of a breast according to an exemplary embodiment;

FIG. 6(b) is a table illustrating image-capture angles depending on the density of a breast according to an exemplary embodiment;

FIG. 6(c) is a table illustrating image-capture angles depending on the thickness and density of a breast according to an exemplary embodiment;

FIG. 7(a) is a table illustrating the number of image-capture operations depending on the thickness of a breast according to an exemplary embodiment;

FIG. 7(b) is a table illustrating the number of image-capture operations depending on the density of a breast according to an exemplary embodiment;

DETAILED DESCRIPTION

Figure 1:
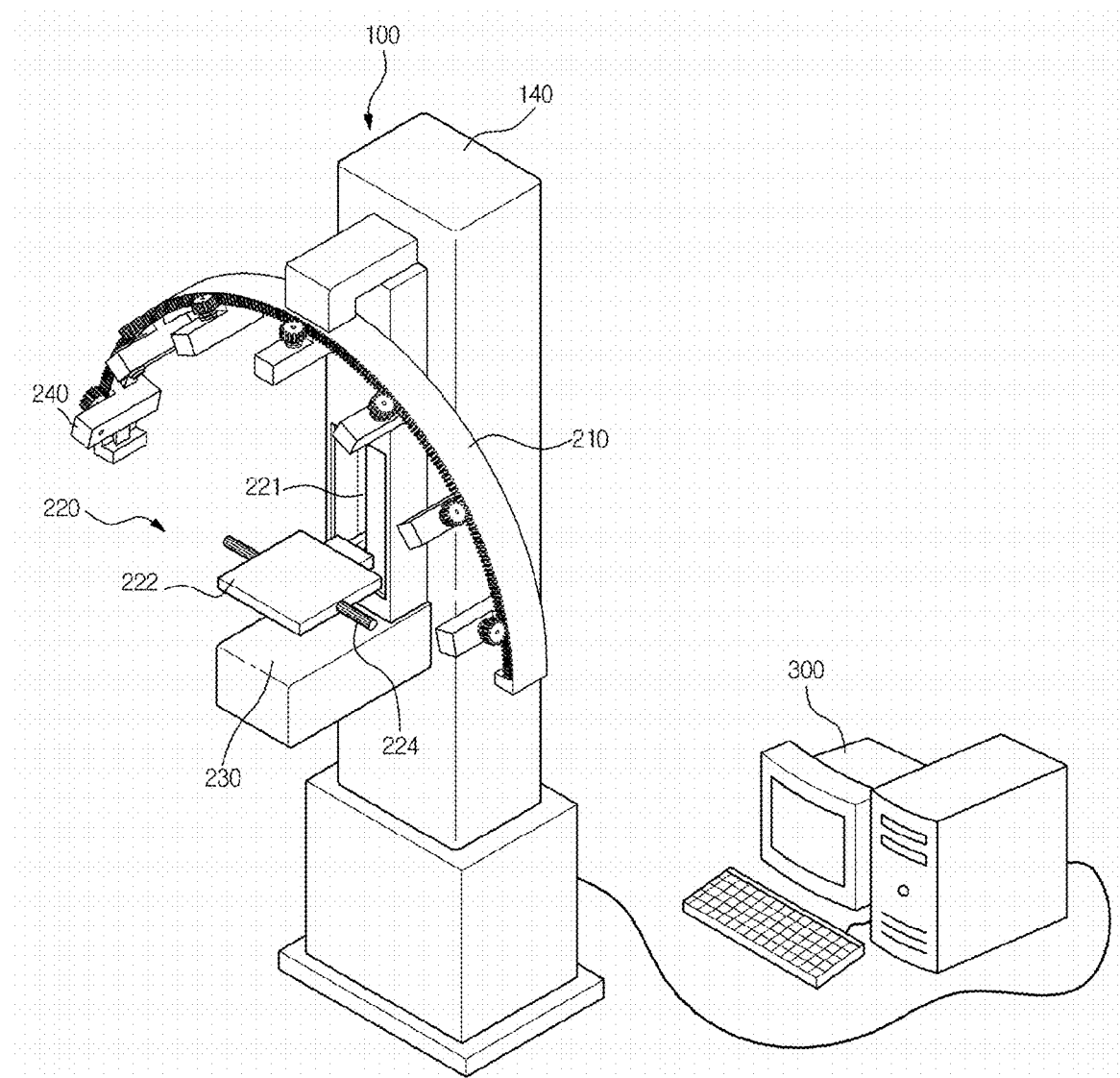
FIG. 1 is a perspective view of an X-ray imaging apparatus according to an exemplary embodiment.

Reference will now be made in detail to the exemplary embodiments of the present disclosure, examples of which are illustrated in the accompanying drawings, wherein like reference numerals refer to like elements throughout.

Hereinafter, exemplary embodiments of an X-ray generation module, an X-ray imaging apparatus, and an X-ray imaging method will be described in detail. In the following description, the X-ray imaging apparatus will be exemplary described as a tomosynthesis system, although it is understood that the X-ray imaging apparatus is not limited to being implemented as a tomosynthesis system.

Figure 2:
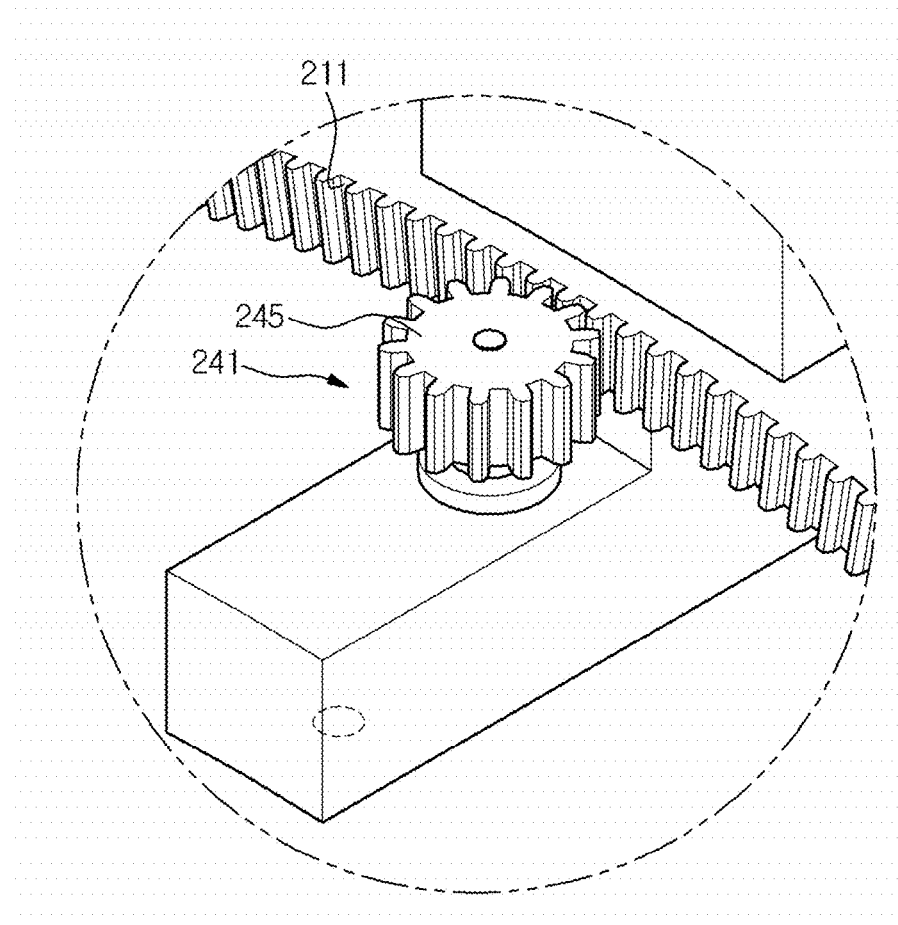
FIG. 2 is an enlarged view of an X-ray generation module of FIG. 1.
Figure 3:
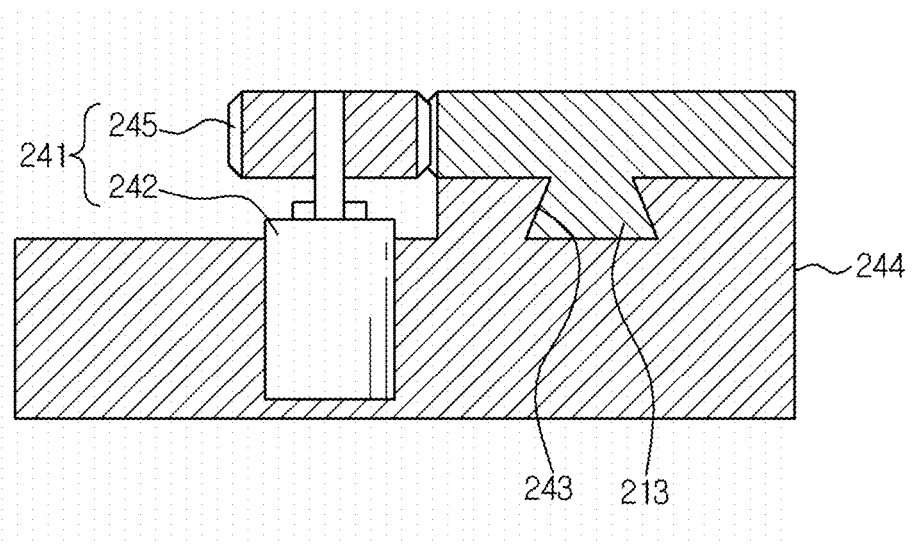
FIG. 3 is a sectional view of the X-ray generation module of FIG. 1.

FIGS. 1 to 3 illustrate an X-ray imaging apparatus according to an exemplary embodiment.

Referring to FIGS. 1 to 3, the X-ray imaging apparatus includes a gantry 100 and an inspector workstation 300.

The gantry 100 includes a main body 140, a transfer member 210 secured to the main body 140, and a plurality of X-ray generation modules 240 configured to move along the transfer member 210. A variety of electronic parts configured for X-ray generation and connection wires connecting the electronic parts are accommodated in the main body 140.

The transfer member 210 is a semi-circular elongated plate, and is provided at a front end thereof with a rack gear 211. A guide protrusion 213 having a dovetail shape is formed at a lower surface of the transfer member 210 to guide movement of the plurality of X-ray generation modules 240. The guide protrusion 213 is fitted into a guide groove 243 formed in each X-ray generation module 240.

Each X-ray generation module 240 includes a housing 244 in which electronic parts that are configured for X-ray generation and are not located in the main body 140 are accommodated, connection wires connecting the electronic parts, a moving unit 241 to move the housing 244, and a filter unit 225. An electric cable is connected to the rear side of the housing 244 to receive power from the main body 140. The moving unit 241 includes a pinion gear 245 rotatably engaged with the rack gear 211, and a transfer motor 242 to rotate the pinion gear 245. According to exemplary embodiments, each X-ray generation module 240 is fabricated as a small and light module.

Although the X-ray generation module 240 has been exemplarily described above as being moved using the rack gear 211 and the pinion gear 245, according to other exemplary embodiments, the X-ray generation module 240 may be moved on the transfer member 210 using other methods, such as a linear motor, etc.

X-rays are generated as a tube voltage is applied to a cathode (not shown) of an X-ray tube (not shown) and a tube current flows through a filament (not show) of the X-ray tube. In this case, the tube voltage and tube current may differ between X-ray imaging apparatuses. In the present exemplary embodiment, a tube voltage of 20~50 kVp (where Vp may hereinafter refer to peak voltage) and a tube current of 10~120 mAs are given by way of example.

The tube voltage has an effect on the quantity of X-rays generated in the X-ray tube and energy of the X-rays (which determines transmittance of the X-rays). If the tube voltage increases, the peak of an X-ray spectrum increases and movement in a high-energy direction occurs. As result, the number of photons generated in the X-ray tube increases and the energy of photons increases as a tube voltage increases.

The tube current has an effect on the quantity of X-rays generated in the X-ray tube. If the tube current increases, the peak of an X-ray spectrum increases and movement in a low-energy or high-energy direction does not occur. As a result, the number of photons generated in the X-ray tube increases as the tube current increases.

An anode (not shown) is a portion with which electrons emitted from the cathode (filament) collide to generate X-rays. X-rays differ according to a constituent material of the anode. For example, if the anode is formed of tungsten, an X-ray spectrum generated from the anode exhibits a gentle ascending and descending graph, the peak of about 24 keV (electron volts) under the condition of a tube voltage of 42 kVp. If the anode is formed of molybdenum, an X-ray spectrum generated from the anode exhibits a spike-shaped graph, the peak of about 17 keV (electron volts) under the condition of a tube voltage of 42 kVp.

The filter unit 225 includes at least one filter which is installed such that the at least one filter may be manually or automatically replaced with another filter. When X-rays pass through the filter, the peak of an X-ray spectrum is lowered and movement in a high-energy direction occurs. Thus, the filter serves to reduce the number of photons (in particular, low-energy photons) and increase the energy of photons. In this case, a reduction rate in the number of photons and an increase rate in the energy of photons differ according to the kind of the filter.

For example, an X-ray spectrum generated when using a Cu filter exhibits a pointed graph having a peak of 10 keV, and an X-ray spectrum generated when using an Al filter exhibits a graph having a peak of about 7 keV which gently descends in a high-energy direction.

The X-ray generation module employed in the present exemplary embodiment may include an X-ray tube in which the cathode is implemented as a Carbon Nano Tube (CNT) instead of the above-described filament. The X-ray tube that adopts a CNT as a cathode consists of a cathode (not shown), a gate (not shown) spaced apart from the cathode (not shown), and an anode (not shown) located opposite to the cathode.

The cathode includes a CNT film support (for example, T0-5 header) (not shown), and a CNT film (not shown) deposited on the CNT film support. The CNT film support is grounded.

The gate is electrically insulated and may be implemented in the form of a mesh. Thus, electrons discharged from the CNT film reach the anode through holes of the mesh.

The electrons discharged from the cathode collide with the anode to generate X-rays. The X-rays differ according to a constituent material of the anode.

The X-rays are generated when a current is applied to the cathode, a gate voltage is applied to the gate, and an anode voltage is applied to the anode. The gate voltage extracts the electrons from the CNT film.

The quantity of X-rays generated from the anode changes according to a voltage difference between the gate and the cathode, and the energy (e.g., transmittance) of X-rays generated from the anode changes according to a voltage difference (e.g., tube voltage) between the cathode and the anode.

If the voltage difference between the gate and the cathode increases, the peak of an X-ray spectrum increases and movement in a high-energy direction occurs. As a result, the number of photons generated from the anode increases and the energy of photons increases as a voltage difference between the cathode and the anode increases.

An X-ray tube implementing a CNT has already been commercialized by several companies (for example, an X-ray tube implementing a CNT was launched by the U.S. company MOXTEK® in 2001). In addition, the X-ray tube having the CNT is a small and light tube having a millimeter-scale diameter. Thus, the X-ray generation module of the present exemplary embodiment including the X-ray tube is also small and light.

A movement range of the X-ray generation module 240 is determined based on image-capture angles and positions and a number of image-capture operations that will be described hereinafter.

An X-ray detector 230 is attached to a front surface of the main body 140 at a position below the transfer member 210 which is exemplarily implemented in the form of a transfer rail. The X-ray detector 230 is configured to detect X-rays having passed through a subject, e.g., a breast. A compression unit 220 is located above the X-ray detector 230 to push the subject toward the X-ray detector 230. The compression unit 220 includes a compression panel 222 and a compression panel guide 221.

The compression panel 222 is movable, for example, in an upward or downward direction. The compression panel 222 applies pressure to the subject when moved downward. The compression panel 222 may be manually moved by the user using a compression panel handle 224, or may be automatically moved via a compression panel movement motor (223 in FIG. 4) installed in the compression panel guide 221.

The compression panel guide 221 is configured to guide the compression panel 222 during movement of the compression panel 222, and the compression panel movement motor (223 in FIG. 4) to move the compression panel 222 is installed in the compression panel guide 221.

The inspector workstation 300 displays and/or stores an X-ray image transmitted from the gantry 100.

Figure 4:
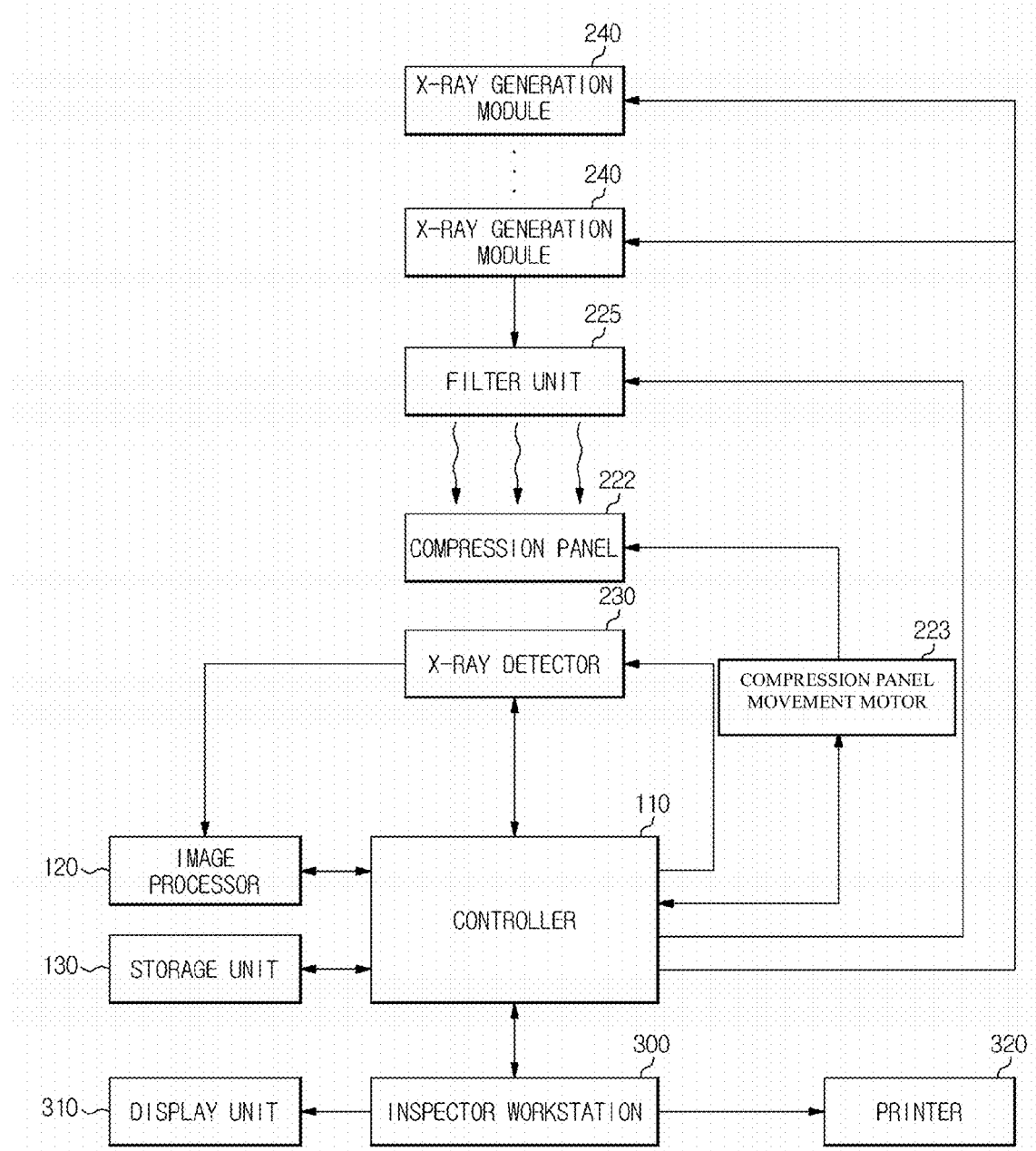
FIG. 4 is a control block diagram of the X-ray imaging apparatus according to an exemplary embodiment.

FIG. 4 is a control block diagram of the X-ray imaging apparatus according to an exemplary embodiment.

As illustrated in FIG. 4, the X-ray imaging apparatus, in addition to the constituent elements illustrated in FIGS. 1 to 3, includes an image processor 120 to acquire an X-ray image from X-rays detected by the X-ray detector 230, a storage unit 130 in which a plurality of image capture condition tables is stored, a controller 110 to control general operations of the X-ray imaging apparatus, a display unit 310 to display an X-ray image, and a printer 320 to print an X-ray image, the display unit 310 and the printer 320 being implemented as separate appliances connected to the inspector workstation 300.

The image processor 120 reads out electric signals of the X-ray detector 230 to acquire an image signal. The image processor 120 generates an X-ray image via reversion of the image signal (for example, via flat field correction). The image processor 120 generates a histogram of the acquired X-ray image. The image histogram is a graph representing brightness distribution of the X-ray image.

As the subject of the present exemplary embodiment, a breast is located in front of a muscle bed, and consists of fibrous tissues constituting the periphery of the breast for shape maintenance, adipose tissues distributed throughout the breast, mammary tissues for generation of breast milk, vascular tissues which function as movement passages of breast milk, etc. Of these tissues, tissues related to generation and supply of breast milk, such as mammary tissues and vascular tissues which function as movement passages of breast milk, are referred to as real tissues of the breast. Generally, the real tissues are primarily composed of protein components.

Protein has a greater density than fat and absorbs a greater quantity of X-rays than fat when exposed to X-rays. Thus, when a breast having a great quantity of real tissues is irradiated with X-rays to acquire an X-ray image and the X-ray image is represented by a histogram, a graph having a low left side and a high right side is generated. Conversely, when a breast having a great quantity of fat tissues is irradiated with X-rays to acquire an X-ray image and the X-ray image is represented by a histogram, a graph having a high left side and a low right side is generated.

Figure 5:
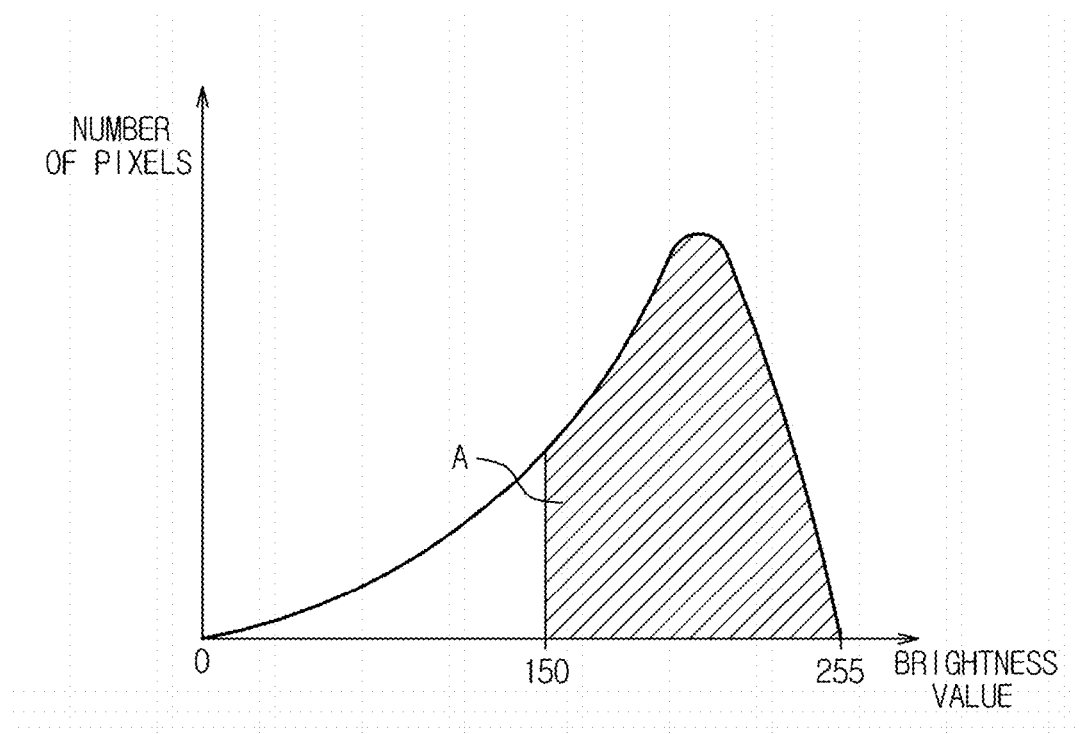
FIG. 5 is a histogram of a pre-shot image according to an exemplary embodiment.

FIG. 5 is a histogram of an X-ray image. In FIG. 5, the X-axis represents a brightness value from 0 to 255 and the Y-axis represents the number of pixels corresponding to each brightness value. As mentioned above, as the brightness value approaches 0, this indicates that pixels corresponding to the brightness value are becoming darker. Conversely, as the brightness value approaches 255, this indicates that pixels corresponding to the brightness value are becoming brighter.

Referring to FIG. 5, it will be appreciated that the number of bright pixels is greater than the number of dark pixels. Accordingly, it will be appreciated that a breast represented by the image histogram of FIG. 5 contains more real tissues than fat tissues.

The storage unit 130 stores image-capture condition tables upon X-ray imaging. Image capture conditions are set differently according to at least one of the thickness and density of a breast compressed by the compression panel 222. The image capture conditions include, for example, an image-capture angle, an image-capture position, the number of image-capture operations to be performed, tube voltage, a constituent material of the filter, a constituent material of the anode, etc. Thus, the storage unit 130 stores a table regarding image-capture angles (see FIG. 6($c$)), a table regarding the number of image-capture operations (see FIG. 7($c$)), a table regarding an image-capture position, a tube voltage/filter table (see FIG. 9), and an anode table. It is understood by those skilled in the art that various other image capture conditions may be implemented in accordance with exemplary embodiments.

The thickness of a breast may be acquired by detecting a position of the compression panel 222. The position of the compression panel 222 may be detected by a sensor (not shown) attached to the compression panel guide 221 which is configured to detect the position of the compression panel 222, or by monitoring the compression panel movement motor 223 that moves the compression panel 222.

The density of a breast refers to the percentage of real tissues in the breast. The density of a breast may be acquired via various methods. In one example, the density of a breast may be acquired by calculating a ratio of the overall area of a breast to the area of real tissues displayed in an X-ray image.

According to an exemplary embodiment, the overall area of the breast may be acquired via integration of an X-ray image histogram, and the area of real tissues may be acquired via integration of a particular region where a brightness value of a pixel exceeds a threshold value (for example, a region where the brightness value is 150 or more within a range of 0~255 (A in FIG. 5)) in a graph. In addition, the density of a breast may be calculated according to the following: (an integral value of a region where a brightness value is a threshold value or more/an integral value of the overall image histogram)*100(%). It is understood that other techniques may be used to calculate the density of a breast according to other exemplary embodiments.

An image-capture angle is an X-ray emission range of each X-ray generation module 240 that is moving on the transfer rail 210. In the present exemplary embodiment, the image-capture angle is an angle defined between a line that connects a left outermost position, to which a leftmost X-ray generation module 240 will move, to the center of a surface of the X-ray detector 230 and a line that connects a rightmost position, to which a rightmost X-ray generation module 240 will move, to the center of a surface of the X-ray detector 230.

The image-capture angle of the present exemplary embodiment is divided into left and right angles on the basis of a vertical center line (a line passing the center of the transfer rail 210 and the center of the X-ray detector 230).

For example, assuming that the image-capture angle is 100°, the left outermost position to which the leftmost X-ray generation module 240 will move is a position spaced leftward by 50° on the basis of the vertical center line, and the right outermost position to which the rightmost X-ray generation module 240 will move is a position spaced rightward by 50° on the basis of the vertical center line.

The image-capture angle may change according to the thickness of a breast as illustrated in an image-capture angle table of FIG. 6(a). That is, the image-capture angle increases as a breast thickness increases, and decreases as a breast thickness decreases. For example, the image-capture angle is 40° if a breast thickness is within a range of 46~55 mm, and is 60° if a breast thickness is within a range of 56~75 mm.

The image-capture angle may change according to the density of a breast as illustrated in an image-capture angle table of FIG. 6(b). That is, the image-capture angle increase as a breast density increases, and decreases as a breast density decreases. For example, the image-capture angle is 40° if a breast density is within a range of 31~40%, and is 60° if a breast density is within a range of 41~60%.

Further, the image-capture angle may change according to both the thickness and density of a breast as illustrated in an image-capture angle table of FIG. 6(c). That is, the image-capture angle increases as a breast thickness and density increase, and decreases as a breast thickness and density decrease. For example, the image-capture angle is 40° if a breast thickness and density are respectively within a range of 26~35 mm and within a range of 31~40%, and is 60° if a breast thickness and density are within a range of 36~45 mm and within a range of 41~50%.

By changing the image-capture angle based on at least one of the thickness and density of a breast, an image capture operation may be performed, at a wide angle, even on a thick and dense breast, which enables acquisition of 3D X-ray images having low blur and high resolution in a depth direction of a breast.

The number of image-capture operations is the sum of the number of X-ray emissions emitted by the plurality of X-ray generation modules 240 within the above-described image-capture angle. For example, if the number of image-capture operations is 21, the plurality of X-ray generation modules 240 emits X-rays to the subject, e.g., a breast, twenty-one times while moving within the image-capture angle. In this case, an X-ray image is acquired whenever X-rays are emitted, and consequently the number of image-capture operations is equal to the number of X-ray images acquired by imaging. Accordingly, in the present exemplary embodiment, it is contemplated that setting of the number of image-capture operations is equal to setting of the number of X-ray images to be acquired. It is understood that other exemplary embodiments are not limited to setting the number of image-capture operations to be equal to the number of X-ray images to be acquired.

The number of image-capture operations may change according to the thickness of a breast as illustrated in a table regarding the number of image-capture operations shown in FIG. 7(a). That is, the number of image-capture operations increases as a breast thickness increases, and decreases as a breast thickness decreases. For example, the number of image-capture operations is set to 21 if a breast thickness is within a range of 46~55 mm, and is set to 25 if a breast thickness is within a range of 56~75 mm.

The number of image-capture operations may change according to the density of a breast as illustrated in a table regarding the number of image-capture operations shown in FIG. 7(b). That is, the number of image-capture operations increases as a breast density increases, and decreases as a breast density decreases. For example, the number of image-capture operations is set to 21 if a breast density is within a range of 31~40%, and is set to 25 if a breast density is within a range of 41~60%.

Figure 7C:
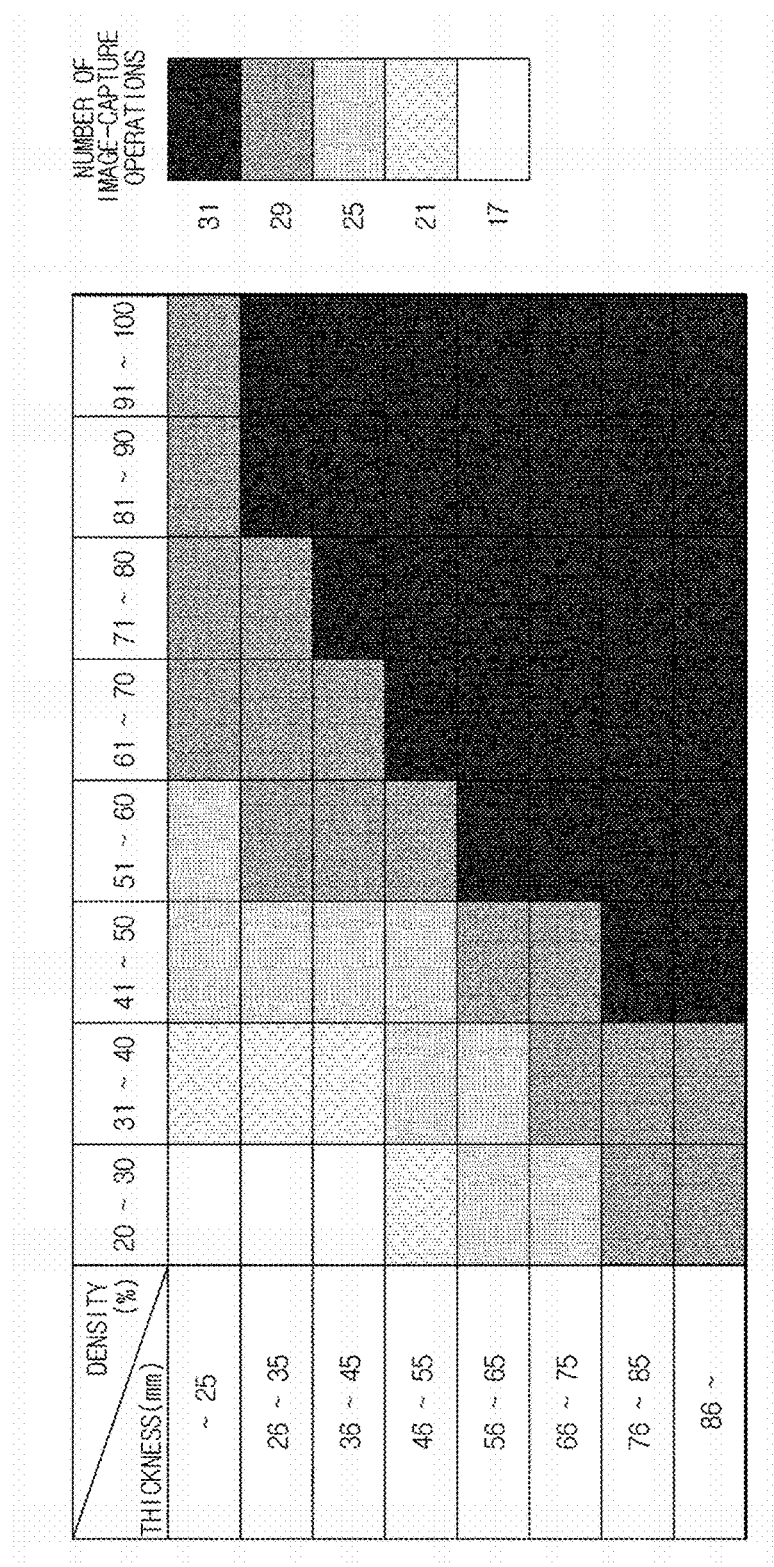
FIG. 7(c) is a table illustrating the number of image-capture operations depending on the thickness and density of a breast according to an exemplary embodiment.

The number of image-capture operations may change according to both the thickness and density of a breast as illustrated in a table regarding the number of image-capture operations shown in FIG. 7(c). That is, the number of image-capture operations increases as a breast thickness and density increase, and decreases as a breast thickness and density decrease. For example, the number of image-capture operations is set to 21 if a breast thickness and density are respectively within a range of 26~35 mm and within a range of 31~40%, and is set to 60° if a breast thickness and density are respectively within a range of 36~45 mm and within a range of 41~50%.

By changing the number of image-capture operations based on at least one of the thickness and density of a breast, a greater number of X-ray images are acquired even in the case of a thick and dense breast, as compared to conventional techniques, which enables acquisition of 3D X-ray images having a high resolution.

An image-capture position refers to a position where each X-ray generation module 240 emits X-rays. According to an exemplary embodiment, a distance between two image-capture positions is set to a value acquired by dividing the image-capture angle by the number of image-capture operations. For example, if the image-capture angle is 50° and the number of image-capture operations is 25, the distance between two image-capture positions is 50/25=2°. Therefore, positions sequentially spaced apart from one another by 2° (which is exemplarily defined as an angle between a line connecting one image-capture position to the center of a surface of the X-ray detector 230 and a line connecting another image-capture position to the center of a surface of the X-ray detector 230) are selected from among image-capture positions on the vertical center line.

Alternatively, distances between every two image-capture positions may differ. A distance between two image-capture positions in a central region of the image-capture angle (defined by an angle between the vertical center line and a line connecting the center of a surface of the X-ray detector to a left or right X-ray generation module, which corresponds to a threshold angle, for example, 12.5° in FIG. 8) may differ from a distance between two image-capture positions in a peripheral region of the image-capture angle (a region except for the central region of the image-capture angle).

Figure 8:
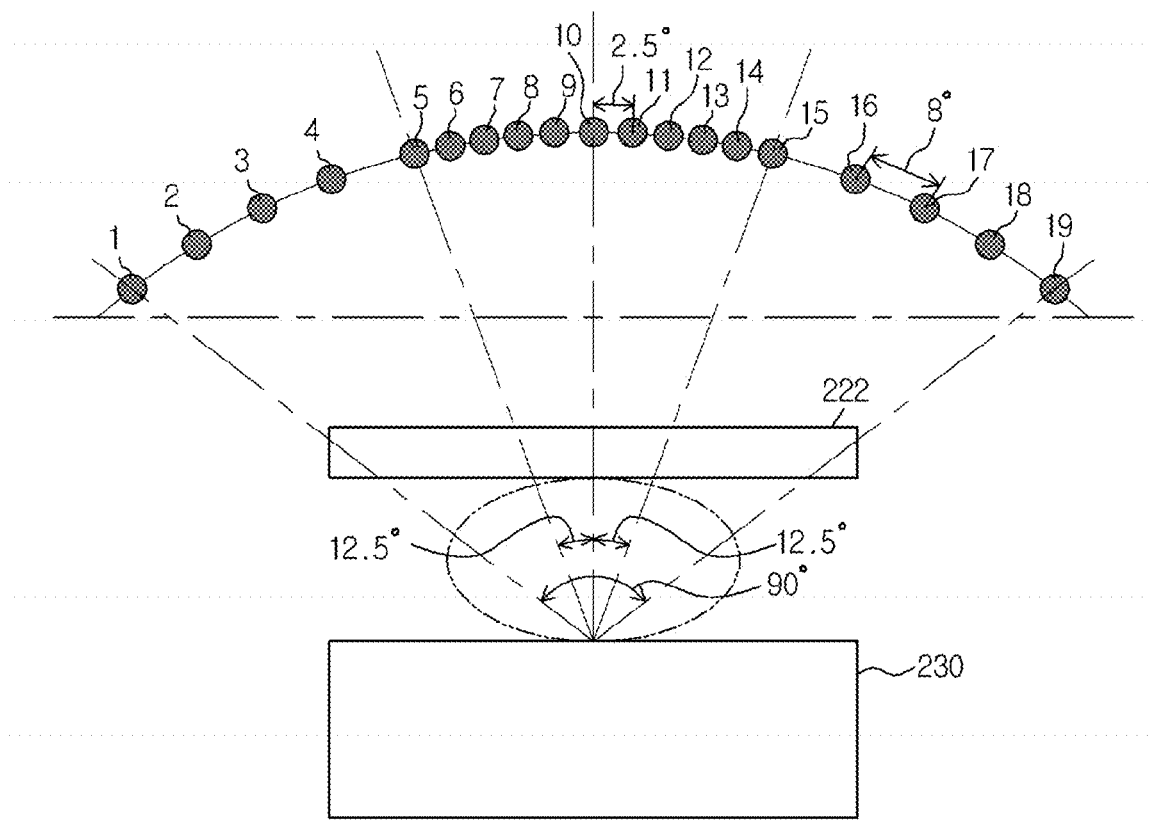
FIG. 8 is a view illustrating image-capture positions according to an exemplary embodiment.

For example, as illustrated in FIG. 8, if the image-capture angle is 90° and the number of image-capture operations is 19, X-rays are emitted eleven times at image-capture positions (from position No. 5 to position No. 15 in FIG. 8) sequentially spaced apart from one another by 2.5° to acquire eleven X-ray images within a range of 12.5° leftward and rightward (central region) on the basis of a virtual vertical center line. Also, X-rays are emitted eight times at image-capture positions (from position No. 1 to position No. 4 and position No. 16 to position No. 19) sequentially spaced apart from one another by 8° to acquire eight X-ray images within a left range of 12.6°~45° and a right range of 12.6°~45° (peripheral region). In FIG. 8, each point represents an image-capture position, and each number is an image-capture position number.

The image-capture positions may be determined based on various factors, for example, based on the thickness or density of a breast. For example, as the thickness or density of a breast increases, a distance between the image-capture positions in the central region becomes narrower than a distance between the image-capture positions in the peripheral region, which enables acquisition of a high-resolution X-ray image. The image-capture position table may be prepared based on various factors, such as the density of a breast, etc.

The definitions and effects of the tube voltage and the filter material have been mentioned above with respect to FIGS. 1 to 3. The tube voltage and the filter material have an effect on the energy of X-rays and the quantity of photons. Thus, the tube voltage and the filter material may be changed if at least one of the thickness and density of a breast is changed, which enables acquisition of a high-resolution 3D X-ray image.

Figure 9:
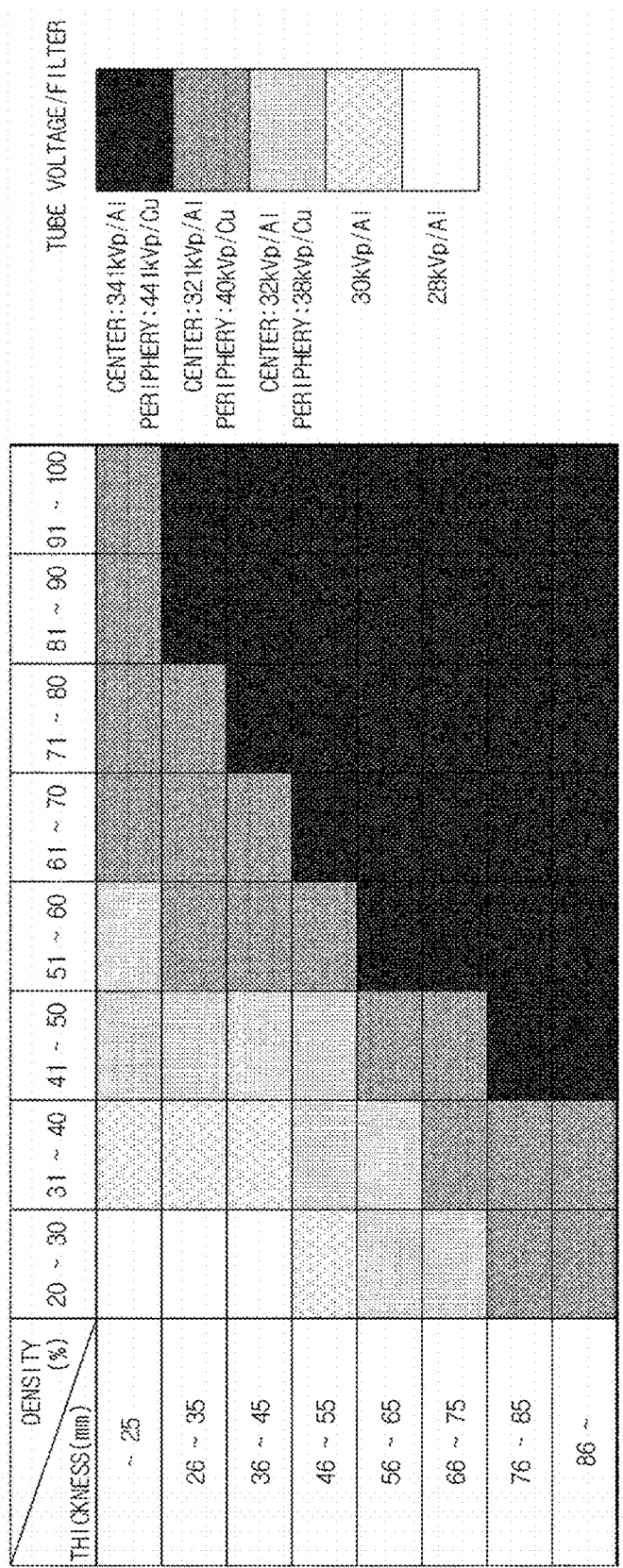
FIG. 9 is a table illustrating tube voltage/filter depending on the thickness and density of a breast according to an exemplary embodiment.

For example, the tube voltage/filter table of FIG. 9 shows that the tube voltage and the filter material may be differently set upon performing an image capture operation if the thickness and density of a breast are changed. That is, as illustrated in FIG. 9, if the thickness of a breast is within a range of 26~35 mm and the density of a breast is within a range of 31~40%, the tube voltage is 30 kVp and the filter is formed of aluminum (Al). As another example, if the thickness of a breast is within a range of 36~45 mm and the density of a breast is within a range of 41~50%, the tube voltage is 32 kVp in the central region and is 38 kVp in the peripheral region and the filter is formed of aluminum (Al) in the central region and copper (Cu) in the peripheral region.

As illustrated in the tube voltage/filter table of FIG. 9, if a breast is thick and dense, the tube voltage and the filter material in the central region differ from the tube voltage and the filter material in the peripheral region during image capture. That is, if a breast is thick and dense, the tube voltage/filter table is constructed such that the central region and the peripheral region have different tube voltages and different filter materials.

By varying the tube voltage and the filter material based on at least one of the thickness and density of a breast, even if a breast is thick and dense, X-rays having energy and a quantity of photons suitable for breast tissues are generated, which enables acquisition of a high-resolution X-ray image.

The role of the anode has been mentioned above with respect to FIGS. 1 to 3. If a material of the anode is changed as described above, the energy of X-rays is changed, and thus the material of the anode may be differently set based on the thickness and density of a breast. Accordingly, the anode table may also be prepared based on at least one of the thickness and density of a breast.

Although the above description exemplifies the respective tables stored in the storage unit 130, the preparation criteria of the respective tables may differ from the above description according to other exemplary embodiments. For example, although the present exemplary embodiment describes that, for example, the image-capture angle is changed based on at least one of the thickness and density of a breast, the respective tables may be prepared based on image capture conditions and other factors aside from the thickness and density of a breast. Numerical values proposed in the respective tables may be set differently from the present exemplary embodiment.

The controller 110 performs Automatic Exposure Control (AEC). AEC is a function of automatically controlling X-ray exposure. More specifically, AEC is a function of controlling X-ray exposure by varying image capture conditions based on properties of breast tissues.

The aforementioned properties of tissues include the thickness and density of a breast. The controller 110 checks the thickness of a breast by receiving a sensed value from a sensor that senses a position of the breast compression panel 222, or by monitoring an operation of the compression panel movement motor 223.

Additionally, the controller 110 calculates the density of a breast by analyzing a pre-shot image that will be described hereinafter. The density of a breast, as described above, refers to the percentage of real tissues in a breast. The density of a breast may be calculated via various methods. For example, the density of a breast may be calculated by calculating a ratio of the overall area of a breast to the area of real tissues displayed in an X-ray image.

According to an exemplary embodiment, the overall area of the breast may be acquired via integration of an X-ray image histogram, and the area of real tissues may be acquired via integration of a particular region where a brightness value of a pixel exceeds a threshold value (for example, a region where the brightness value is 150 or more within a range of 0~255 (see threshold value A in FIG. 5)) in the graph. In addition, the density of a breast may be calculated by (an integral value of a region where a brightness value is a threshold value or more/an integral value of the overall image histogram)*100(%). It is understood that other techniques may also be used to calculate the density of a breast.

If properties of tissues are checked, the controller 110 sets image capture conditions of a main-shot that will be described hereinafter based on at least one of the thickness and density of a breast by referring to the respective tables of the storage unit 130. According to an exemplary embodiment, the main-shot refers to an image capture operation to generate an X-ray image for inspection of a breast, such as detection of diseases of a breast. The image capture conditions may include the image-capture angle, the number of image-capture operations (e.g., the number of 2D X-ray images to be captured), the image-capture position, the tube voltage, the filter material, and the anode material.

If the image capture conditions are set, the controller 110 performs a main-shot. During the main-shot, the controller 110 simultaneously drives the X-ray generation modules 240 independently of one another to position the X-ray generation modules 240 at respective image-capture positions, and then sequentially drives the X-ray generation modules 240 to emit X-rays to the subject.

In this case, the movement and image capture operations of the respective X-ray generation modules 240 may be performed in various sequences. For example, if there are seven X-ray generation modules, and the number of image-capture operations and the image-capture position are equal to those in FIG. 8 (that is, the number of image-capture operations is 19 and the image-capture positions differ between the central region and the peripheral region), all the X-ray generation modules move from the image-capture position of No. 1 to the image-capture position of No. 7, and sequentially emit X-rays to the subject.

Next, seven X-ray generation modules move from the image-capture position of No. 8 to the image-capture position of No. 14 and sequentially emit X-rays to the subject. Finally, the left two X-ray generation modules among the seven X-ray generation modules stop, and the right five X-ray generation modules move from the image-capture position of No. 15 to the image-capture position of No. 19 and sequentially emit X-rays to the subject. In this example sequence, since X-rays are emitted a total of nineteen times, a total of nineteen 2D X-ray images may be acquired.

The respective X-ray generation modules may perform image capture operations by moving in a sequence which is different from the above-described sequence. Under the above-described conditions, a middle X-ray generation module among the seven X-ray generation modules moves to the image-capture position of No. 10, the left three X-ray generation modules move to the image-capture positions of No. 7 to No. 9, and the right three X-ray generation modules move to the image-capture positions of No. 11 to No. 13, so as to sequentially irradiate the subject with X-rays.

Next, the X-ray generation module at the image-capture position of No. 10 stops, the left three X-ray generation modules move to the image-capture positions of No. 4 to No. 6, and the right three X-ray generation modules move to the image-capture positions of No. 14 to No. 16, so as to sequentially irradiate the subject with X-rays.

Finally, the X-ray generation module at the image-capture position of No. 10 stops, the left three X-ray generation modules move to the image-capture positions of No. 1 to No. 3, and the right three X-ray generation modules move to the image-capture positions of No. 17 to No. 19, so as to sequentially irradiate the subject with X-rays. As such, X-rays are emitted a total of nineteen times, and thus a total of nineteen 2D X-ray images may be acquired.

Although the respective X-ray generation modules 240 have been described in certain exemplary sequences described above as simultaneously moving to the respective image-capture positions and sequentially emitting X-rays, the respective X-ray generation modules 240 may be driven independently of one another, and therefore one X-ray generation module may move to a next image-capture position while another X-ray generation module emits X-rays to capture an image of the subject.

The respective X-ray generation modules 240, after simultaneously moving to the respective image-capture positions, may initiate X-ray image capture operations after a sufficient standby duration has passed. In this case, the sufficient standby duration is set to a duration for removal of a damping motion that may occur according to movement of each X-ray generation module 240, so as to prevent a blurred 2D image due to the damping motion.

Figure 10:
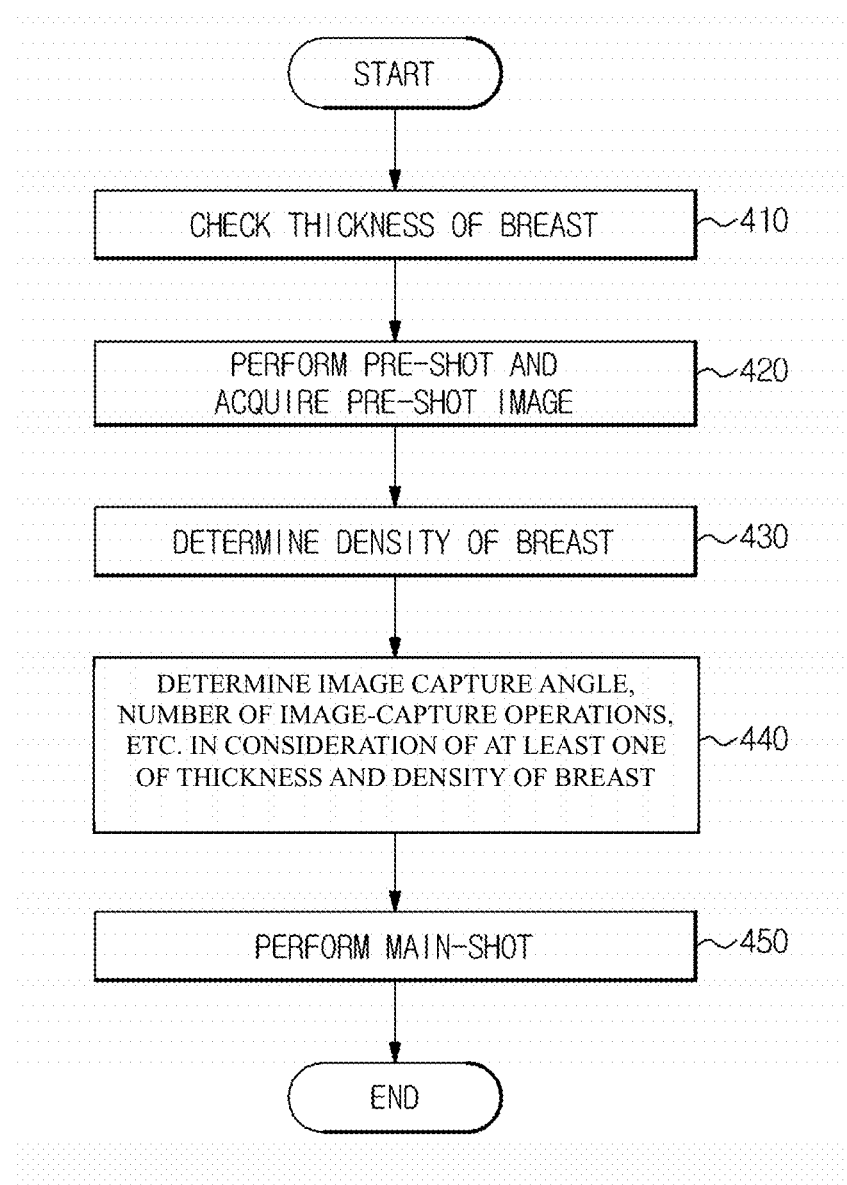
FIG. 10 is a flowchart illustrating an exemplary embodiment of an X-ray imaging method.

Hereinafter, an exemplary embodiment of an X-ray imaging method will be described in detail with reference to FIG. 10.

If a breast of a patient is compressed via downward movement of the compression panel 222 in a state in which the breast is placed on the X-ray detector 230, the controller 110 checks the thickness of the breast at operation 410. The thickness of the breast, as described above, may be acquired according to various techniques, for example, by a sensed value of the sensor that senses a position of the compression panel 222, or by monitoring a rotation of the compression panel movement motor 223.

Next, a middle X-ray generation module 240 among the plurality of X-ray generation modules 240 emits X-rays to perform a pre-shot, and the image processor 120 generates a 2D pre-shot image at operation 420. According to an exemplary embodiment, a pre-shot refers to an operation of capturing an X-ray image required to acquire the density of the breast that is used as a criterion for setting of image capture conditions.

Upon performing the pre-shot, the X-ray generation module 240 emits X-rays once on the vertical center line, and the controller 110 sets image capture conditions, such as tube voltage, tube current, etc., to emit low-dose X-rays to the breast.

Next, the image processor 120 generates a histogram of a pre-shot image. Once the image histogram is generated, the controller 110 acquires an integral value of the overall image histogram and an integral value of a region where the brightness value exceeds a threshold value. A ratio between the two integral values, e.g., (the integral value of the region where the brightness value is a threshold value or more/the integral value of the overall image histogram)*100(%), is acquired and is used to set the density of the breast at operation 430.

Next, the controller 110 determines image capture conditions for a main-shot based on at least one of the thickness and density of the breast at operation 440. The image capture conditions include, for example, an image-capture angle, an image-capture position, the number of image-capture operations, a tube voltage, a filter material, and an anode material.

The controller 110 sets the image-capture angle, the image-capture position, the number of image-capture operations, the tube voltage, the filter material, and the anode material with reference to tables regarding the image-capture angle, the number of image-capture operations, the image-capture position, the tube voltage, the filter material, and the anode material stored in the storage unit 130.

Once the image capture conditions for the main-shot are set, the plurality of X-ray generation modules 240 moves to respective image-capture positions and sequentially emits X-rays, thereby performing the main-shot. The image processor 120 generates a plurality of 2D main-shot images, and generates a 3D X-ray image based on the plurality of 2D main-shot images.

Although the main-shot is performed based on the set image capture conditions in the present exemplary embodiment, the set image capture conditions may be displayed to an inspector (e.g., medical professional) to provide the inspector with a chance to correct the displayed image capture conditions.

For example, the controller 110 may set the image capture conditions for the main-shot, and control the inspector workstation 300 to display the image capture conditions. In addition, under control of the controller 110, a message to inquire whether to correct the set image capture conditions may be displayed.

If the inspector inputs the changed image capture conditions to the inspector workstation 300, the controller 110 receives the changed image-capture conditions from the inspector workstation 300 and controls the main-shot based on the image capture conditions.

As is apparent from the above description, an X-ray imaging apparatus and an X-ray imaging method according to exemplary embodiments may attenuate blurring of a 2D image caused by a damping motion that occurs in a step-and-shot method due to X-ray generation module momentum.

Further, the X-ray imaging apparatus and an X-ray imaging method according to exemplary embodiments may set image capture conditions which are optimized for each subject, thereby preventing an unnecessary increase in the number of image-capture operations to be performed for diagnosing the subject, and consequently preventing an unnecessary increase in patient X-ray exposure.

Although the exemplary embodiments of the present disclosure have been shown and described, it would be appreciated by those skilled in the art that changes may be made in these exemplary embodiments without departing from the principles and spirit of the disclosure, the scope of which is defined in the claims and their equivalents.

What is claimed is:

1. An X-ray imaging apparatus comprising:
a main body;
a transfer rail secured to the main body;
a plurality of X-ray generation modules configured to emit X-rays to a subject, the X-ray generation modules being configured to move independently of one another;
an X-ray detector configured to detect a plurality of X-rays emitted from the plurality of X-ray generation modules and which have passed through the subject; and
an image processor configured to acquire a plurality of X-ray images from the plurality of detected X-rays,
wherein the transfer rail comprises a rack gear and a guide protrusion to guide movement of the plurality of X-ray generation modules.

2. The apparatus according to claim 1,
wherein the plurality of X-ray generation modules is configured to move along the transfer rail.

3. The apparatus according to claim 2, wherein each of the X-ray generation modules comprises a moving unit configured to move each X-ray generation module independently.

4. The apparatus according to claim 3,
wherein the moving unit of each X-ray generation module comprises a pinion gear engaged with the rack gear, and a transfer motor to rotate the pinion gear, and
wherein each X-ray generation module has a guide groove into which the guide protrusion is fitted.

5. An X-ray imaging apparatus comprising:
a plurality of X-ray generation modules configured to emit X-rays to a subject, the X-ray generation modules being configured to move independently of one another;
an X-ray detector configured to detect X-rays emitted from the plurality of X-ray generation modules and which have passed through the subject;
an image processor configured to acquire a plurality of X-ray images from the plurality of detected X-rays;
a controller configured to independently move the respective X-ray generation modules so as to enable the plurality of X-ray generation modules to irradiate the subject with X-rays at different positions;
a main body; and
a transfer rail secured to the main body,
wherein the plurality of X-ray generation modules is configured to move along the transfer rail, and
wherein the transfer rail comprises a rack gear and a guide protrusion to guide movement of the plurality of X-ray generation modules.

6. An X-ray imaging apparatus comprising:
a plurality of X-ray generation modules configured to emit X-rays to a subject, the X-ray generation modules being configured to move independently of one another;
an X-ray detector configured to detect a plurality of X-rays emitted from the plurality of X-ray generation modules and which have passed through the subject;
an image processor configured to acquire a plurality of X-ray images from the plurality of detected X-rays; and
a controller configured to set image-capture conditions based on at least one of a thickness and a density of the subject, and configured to move at least one X-ray generation module among the plurality of X-ray generation modules according to the image-capture conditions, thereby controlling an image capture operation to capture an image of the subject.

7. An X-ray imaging method comprising:
checking a thickness of a subject;
performing a pre-shot by emitting X-rays from at least one X-ray generation module, among a plurality of X-ray generation modules that are movable independently of one another, to the subject, and acquiring a pre-shot image of the subject based on the pre-shot;
determining a density of the subject by analyzing the acquired pre-shot image;
setting image-capture conditions for a main-shot based on at least one of the thickness and density of the subject; and
performing the main-shot by moving the at least one X-ray generation module among the plurality of X-ray generation modules according to the image-capture conditions, and acquiring a main-shot image based on the main-shot.

8. The method according to claim 7, wherein the image-capture conditions include an image-capture angle, an image-capture position, and a number of image-capture operations.

9. The method according to claim 8, wherein the image-capture angle is set to a greater value as the thickness of the subject increases, and is set to a smaller value as the thickness of the subject decreases.

10. The method according to claim 8, wherein the image-capture angle is set to a greater value as the density of the subject increases, and is set to a smaller value as the density of the subject decreases.

11. The method according to claim 8, wherein the image-capture angle is set to a greater value as the thickness of the subject increases and the density of the subject increases, and is set to a smaller value as the thickness of the subject decreases and the density of the subject decreases.

12. The method according to claim 8, wherein the number of image-capture operations is set to a greater value as the thickness of the subject increases, and is set to a smaller value as the thickness of the subject decreases.

13. The method according to claim 8, wherein the number of image-capture operations is set to a greater value as the density of the subject increases, and is set to a smaller value as the density of the subject decreases.

14. The method according to claim 8, wherein the number of image-capture operations is set to a greater value as the thickness of the compressed subject increases and the density of the subject increases, and is set to a smaller value as the thickness of the compressed subject decreases and the density of the subject decreases.

15. The method according to claim 8, wherein a distance between two neighboring image-capture positions in a central region is set to be different as compared to a distance between two neighboring image-capture positions in a peripheral region of an image capture angular range.

16. The method according to claim 15, wherein the image-capture positions are set such that the distance between the two neighboring image-capture positions in the central region is smaller than the distance between the two neighboring image-capture positions in the peripheral region.

17. The method according to claim 15, wherein a magnitude of a tube voltage and a filter material in the central region are set to be different as compared to a magnitude of a tube voltage and a filter material in the peripheral region.

18. The method according to claim 8, wherein the image-capture conditions further include an anode material.

19. An X-ray imaging apparatus comprising:
a transfer member;
a plurality of X-ray generation modules configured to emit X-rays to a subject, the X-ray generation modules being configured to move independently of one another along the transfer member; and
a controller configured to control the plurality of X-ray generation modules to independently move to respective positions along the transfer member, and, after moving to the respective positions, to emit the X-rays to the subject after a standby duration elapses.

20. The X-ray imaging apparatus according to claim 19, wherein the standby duration corresponds to a duration of time for removal of a damping motion that occurs according to movement of the plurality of X-ray generation modules.

21. The X-ray imaging apparatus according to claim 19, wherein the subject comprises a human female breast.

22. The X-ray imaging apparatus according to claim 21, wherein the respective positions to which the plurality of X-ray generation modules are independently moved are determined according to at least one characteristic of the human female breast.

23. The X-ray imaging apparatus according to claim 22, wherein the at least one characteristic comprises at least one of a thickness of the human female breast and a density of the human female breast.

24. An X-ray imaging method comprising:
performing a pre-shot by emitting X-rays from at least one X-ray generation module, among a plurality of X-ray generation modules that are movable independently of one another, to a subject, and acquiring a pre-shot image of the subject based on the pre-shot;
determining a density of the subject by analyzing the acquired pre-shot image;
setting image-capture conditions for a main-shot based on the density of the subject; and
performing the main-shot by moving the at least one X-ray generation module among the plurality of X-ray generation modules according to the image-capture conditions, and acquiring a main-shot image based on the main shot.

25. An X-ray imaging method comprising:
checking a thickness of a subject;
setting image-capture conditions for a main-shot based on the thickness of the subject; and
performing the main-shot by moving at least one X-ray generation module among a plurality of X-ray generation modules according to the image-capture conditions, and acquiring a main-shot image based on the main-shot.

* * * * *